(12) United States Patent
Kingsley et al.

(10) Patent No.: US 11,925,406 B2
(45) Date of Patent: Mar. 12, 2024

(54) END EFFECTOR ASSEMBLIES FOR SURGICAL INSTRUMENTS

(71) Applicant: Covidien LP, Mansfield, MA (US)

(72) Inventors: Dylan R. Kingsley, Broomfield, CO (US); Crystal A. Adams, Westminster, CO (US); Jason G. Weihe, Longmont, CO (US); William Whitney, Boulder, CO (US); Russell W. Holbrook, Longmont, CO (US); Zachary S. Heiliger, Nederland, CO (US); Curtis M. Siebenaller, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 742 days.

(21) Appl. No.: 17/020,117

(22) Filed: Sep. 14, 2020

(65) Prior Publication Data

US 2022/0079663 A1 Mar. 17, 2022

(51) Int. Cl.
| | |
|---|---|
| *A61B 34/00* | (2016.01) |
| *A61B 18/14* | (2006.01) |
| *A61B 34/37* | (2016.01) |
| *A61B 18/00* | (2006.01) |
| *A61B 34/30* | (2016.01) |

(52) U.S. Cl.
CPC .......... *A61B 18/1445* (2013.01); *A61B 34/37* (2016.02); *A61B 34/74* (2016.02); *A61B 2018/00077* (2013.01); *A61B 2018/00601* (2013.01); *A61B 2018/1455* (2013.01); *A61B 2034/305* (2016.02)

(58) Field of Classification Search
CPC ........ A61B 18/1445; A61B 2018/1455; A61B 2018/00077
See application file for complete search history.

(56) References Cited

U.S. PATENT DOCUMENTS

| | | |
|---|---|---|
| 702,472 A | 6/1902 | Pignolet |
| 2,801,633 A | 8/1957 | Ehrlich |
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| 4,793,218 A | 12/1988 | Jordan et al. |

(Continued)

FOREIGN PATENT DOCUMENTS

| | | |
|---|---|---|
| EP | 2520242 A1 | 11/2012 |
| EP | 2777586 A1 | 9/2014 |
| WO | 2016045041 A1 | 3/2016 |

OTHER PUBLICATIONS

Extended European Search Report for Application No. 21196707.0 dated Feb. 1, 2022.

(Continued)

*Primary Examiner* — Tammie K Marlen
(74) *Attorney, Agent, or Firm* — Carter, DeLuca & Farrell LLP

(57) ABSTRACT

A surgical end effector assembly includes first and second jaw members configured to grasp tissue. Each of the first and second jaw members includes a proximal flange portion and a distal body portion. The proximal flange portions are pivotably coupled to one another to move the distal body portions between a spaced-apart position and an approximated position.

18 Claims, 9 Drawing Sheets

(56) References Cited

U.S. PATENT DOCUMENTS

| | | |
|---|---|---|
| D299,413 S | 1/1989 | DeCarolis |
| 5,100,506 A | 3/1992 | Sturtevant et al. |
| 5,242,456 A | 9/1993 | Nash et al. |
| D343,453 S | 1/1994 | Noda |
| 5,302,234 A | 4/1994 | Grace et al. |
| 5,317,938 A | 6/1994 | de Juan, Jr. et al. |
| D348,930 S | 7/1994 | Olson |
| D349,341 S | 8/1994 | Lichtman et al. |
| D354,564 S | 1/1995 | Medema |
| 5,383,471 A | 1/1995 | Funnell |
| 5,395,364 A | 3/1995 | Anderhub et al. |
| D358,887 S | 5/1995 | Feinberg |
| 5,431,667 A | 7/1995 | Thompson et al. |
| 5,486,185 A | 1/1996 | Freitas et al. |
| 5,486,189 A | 1/1996 | Mudry et al. |
| 5,522,830 A | 6/1996 | Aranyi |
| 5,522,839 A | 6/1996 | Pilling |
| 5,539,973 A | 7/1996 | Smith et al. |
| 5,571,129 A | 11/1996 | Porter |
| 5,620,447 A | 4/1997 | Smith et al. |
| 5,626,609 A | 5/1997 | Zvenyatsky et al. |
| D384,413 S | 9/1997 | Zlock et al. |
| 5,707,392 A | 1/1998 | Kortenbach |
| 5,716,374 A | 2/1998 | Francese et al. |
| 5,752,973 A | 5/1998 | Kieturakis |
| H1745 H | 8/1998 | Paraschac |
| 5,792,135 A | 8/1998 | Madhani et al. |
| 5,833,692 A | 11/1998 | Cesarini et al. |
| D402,028 S | 12/1998 | Grimm et al. |
| 5,848,986 A | 12/1998 | Lundquist et al. |
| D408,018 S | 4/1999 | McNaughton |
| D416,089 S | 11/1999 | Barton et al. |
| 6,013,028 A | 1/2000 | Jho et al. |
| D424,694 S | 5/2000 | Tetzlaff et al. |
| D425,201 S | 5/2000 | Tetzlaff et al. |
| 6,117,158 A | 9/2000 | Measamer et al. |
| H1904 H | 10/2000 | Yates et al. |
| 6,202,465 B1 | 3/2001 | Jankoski et al. |
| 6,277,117 B1 | 8/2001 | Tetzlaff et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| 6,817,974 B2 | 11/2004 | Cooper et al. |
| D502,994 S | 3/2005 | Blake, III |
| D509,297 S | 9/2005 | Wells |
| D525,361 S | 7/2006 | Hushka |
| 7,101,371 B2 | 9/2006 | Dycus et al. |
| D531,311 S | 10/2006 | Guerra et al. |
| 7,122,035 B2 | 10/2006 | Canady |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| 7,186,261 B2 | 3/2007 | Prestel |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,267,677 B2 | 9/2007 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,799,028 B2 | 9/2010 | Schechter et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,861,906 B2 | 1/2011 | Doll et al. |
| 7,918,230 B2 | 4/2011 | Whitman et al. |
| D649,249 S | 11/2011 | Guerra |
| D649,643 S | 11/2011 | Allen, IV et al. |
| D661,394 S | 6/2012 | Romero et al. |
| 8,333,765 B2 | 12/2012 | Johnson et al. |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,579,176 B2 | 11/2013 | Smith et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,055,961 B2 | 6/2015 | Manzo et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 9,192,432 B2 | 11/2015 | Larson et al. |
| 9,259,268 B2 | 2/2016 | Behnke et al. |
| 9,265,565 B2 | 2/2016 | Kerr |

(56) References Cited

U.S. PATENT DOCUMENTS

| | | |
|---|---|---|
| 9,265,568 B2 | 2/2016 | Chernov et al. |
| 9,265,569 B2 | 2/2016 | Hart et al. |
| 9,314,295 B2 | 4/2016 | Garrison |
| 9,375,258 B2 | 6/2016 | Kendrick |
| 9,375,263 B2 | 6/2016 | Allen, IV et al. |
| 9,375,282 B2 | 6/2016 | Nau, Jr. et al. |
| 9,381,059 B2 | 7/2016 | Garrison |
| 9,456,870 B2 | 10/2016 | Chernov et al. |
| 9,474,569 B2 | 10/2016 | Manzo et al. |
| 9,486,220 B2 | 11/2016 | Twomey et al. |
| 9,492,221 B2 | 11/2016 | Garrison |
| 9,615,877 B2 | 4/2017 | Tyrrell et al. |
| 9,636,169 B2 | 5/2017 | Allen, IV et al. |
| 9,668,806 B2 | 6/2017 | Unger et al. |
| 9,693,816 B2 | 7/2017 | Orszulak |
| 9,713,493 B2 | 7/2017 | Waaler et al. |
| 9,820,765 B2 | 11/2017 | Allen, IV et al. |
| 9,844,384 B2 | 12/2017 | Chernov et al. |
| 9,956,030 B2 | 5/2018 | Allen, IV et al. |
| 10,117,705 B2 | 11/2018 | Chernov et al. |
| 10,271,897 B2 | 4/2019 | Allen, IV et al. |
| 10,731,740 B1 | 8/2020 | Cui et al. |
| 2002/0058925 A1 | 5/2002 | Kaplan et al. |
| 2002/0062131 A1 | 5/2002 | Gallo |
| 2002/0099371 A1 | 7/2002 | Schulze et al. |
| 2002/0161364 A1 | 10/2002 | Mulier et al. |
| 2002/0177842 A1 | 11/2002 | Weiss |
| 2003/0060816 A1 | 3/2003 | Iida |
| 2003/0125734 A1 | 7/2003 | Mollenauer |
| 2003/0208186 A1 | 11/2003 | Moreyra |
| 2004/0148992 A1 | 8/2004 | Huang |
| 2004/0193153 A1 | 9/2004 | Sartor et al. |
| 2004/0254573 A1 | 12/2004 | Dycus et al. |
| 2005/0090837 A1 | 4/2005 | Sixto, Jr. |
| 2005/0240218 A1 | 10/2005 | Freed et al. |
| 2006/0022015 A1 | 2/2006 | Shelton et al. |
| 2006/0025811 A1 | 2/2006 | Shelton |
| 2006/0052777 A1 | 3/2006 | Dumbauld |
| 2006/0161138 A1 | 7/2006 | Orban et al. |
| 2007/0233052 A1 | 10/2007 | Brock |
| 2008/0015631 A1 | 1/2008 | Lee et al. |
| 2008/0083257 A1 | 4/2008 | Taylor et al. |
| 2008/0134812 A1 | 6/2008 | Murata |
| 2008/0264139 A1 | 10/2008 | Rosenbohm et al. |
| 2008/0319442 A1 | 12/2008 | Unger et al. |
| 2008/0319467 A1 | 12/2008 | Wenchell |
| 2009/0088743 A1 | 4/2009 | Masuda |
| 2009/0182327 A1 | 7/2009 | Unger |
| 2010/0094287 A1 | 4/2010 | Cunningham et al. |
| 2010/0145334 A1 | 6/2010 | Olson et al. |
| 2010/0274265 A1 | 10/2010 | Wingardner et al. |
| 2010/0292691 A1 | 11/2010 | Brogna |
| 2011/0009864 A1 | 1/2011 | Bucciaglia et al. |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2011/0144665 A1 | 6/2011 | Malkowski |
| 2011/0301600 A1 | 12/2011 | Garrison et al. |
| 2012/0022527 A1 | 1/2012 | Woodruff et al. |
| 2012/0215220 A1 | 8/2012 | Manzo et al. |
| 2012/0239034 A1 | 9/2012 | Horner et al. |
| 2012/0265241 A1 | 10/2012 | Hart et al. |
| 2012/0296238 A1 | 11/2012 | Chernov et al. |
| 2012/0296371 A1 | 11/2012 | Kappus et al. |
| 2012/0303026 A1 | 11/2012 | Dycus et al. |
| 2012/0330308 A1 | 12/2012 | Joseph |
| 2013/0022495 A1 | 1/2013 | Allen, IV et al. |
| 2013/0071282 A1 | 3/2013 | Fry |
| 2013/0079774 A1 | 3/2013 | Whitney et al. |
| 2013/0123783 A1 | 5/2013 | Marczyk et al. |
| 2013/0274736 A1 | 10/2013 | Garrison |
| 2013/0304066 A1 | 11/2013 | Kerr et al. |
| 2014/0025071 A1 | 1/2014 | Sims et al. |
| 2014/0276723 A1 | 9/2014 | Parihar et al. |
| 2017/0042560 A1 | 2/2017 | Lee et al. |
| 2017/0150975 A1 | 6/2017 | Bozung |
| 2017/0265951 A1 | 9/2017 | Grover et al. |
| 2017/0273749 A1 | 9/2017 | Grover et al. |
| 2017/0365923 A1 | 12/2017 | Schmutzler et al. |
| 2018/0028271 A1 | 2/2018 | Rockrohr |
| 2018/0071037 A1 | 3/2018 | Grover et al. |
| 2018/0206907 A1 | 7/2018 | Dycus et al. |
| 2018/0310948 A1* | 11/2018 | Stamm ............... A61B 18/1445 |
| 2019/0008600 A1 | 1/2019 | Pedros et al. |
| 2019/0015124 A1 | 1/2019 | Williams et al. |
| 2019/0099227 A1 | 4/2019 | Rockrohr |
| 2019/0274769 A1 | 9/2019 | Perdue et al. |
| 2020/0237453 A1 | 7/2020 | Anglese |
| 2020/0237455 A1 | 7/2020 | Anglese |
| 2020/0246058 A1 | 8/2020 | Traina |
| 2020/0253676 A1 | 8/2020 | Traina |
| 2020/0261166 A1 | 8/2020 | Anglese |
| 2020/0261167 A1 | 8/2020 | Anglese |
| 2020/0261168 A1 | 8/2020 | Anglese |

OTHER PUBLICATIONS

Extended European Search Report for Application No. 21196716.1 dated Feb. 4, 2022.

* cited by examiner

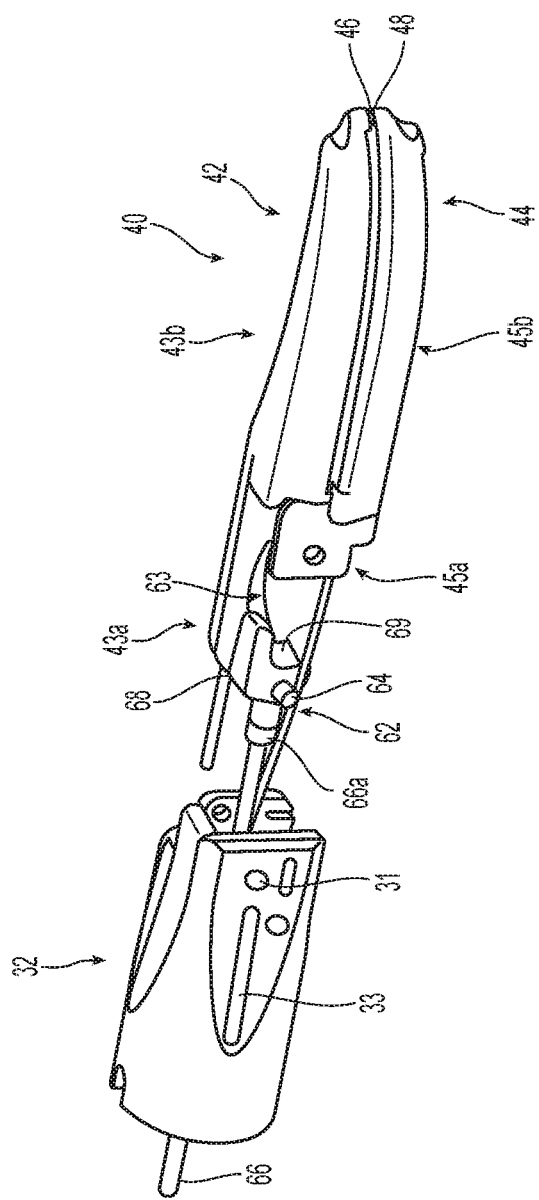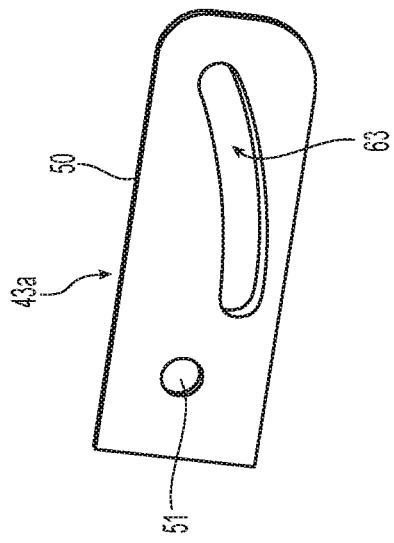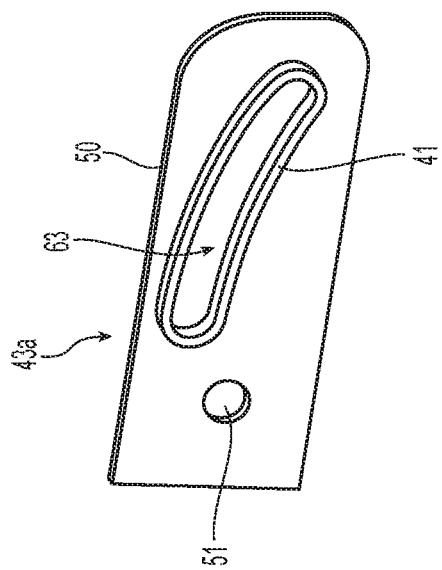

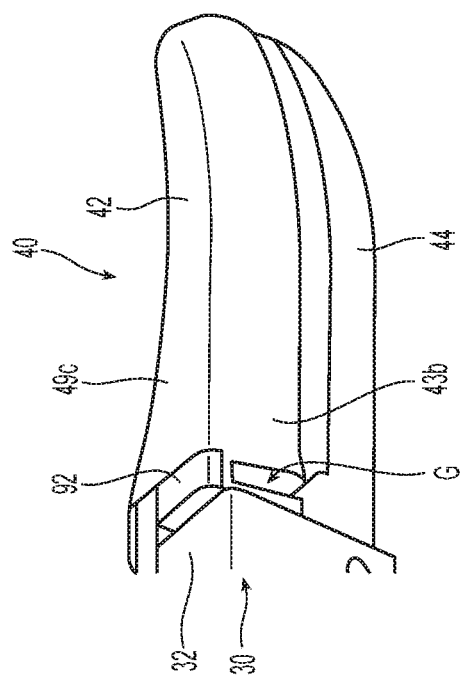
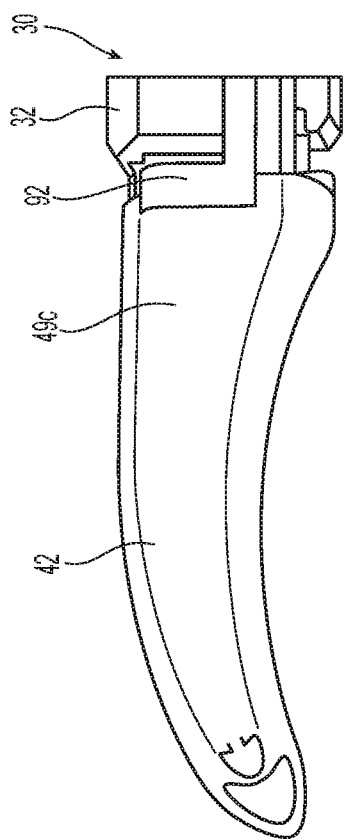

and second jaw members between the spaced-apart and approximated positions. The proximal flange portion of the first jaw member may include a lip extending around the cam slot. The lip may extend tangentially outward from a side surface of a plate-shaped flange of the proximal flange portion.

END EFFECTOR ASSEMBLIES FOR SURGICAL INSTRUMENTS

FIELD

The present disclosure relates to surgical instruments and, more specifically, to end effector assemblies for surgical instruments, such as for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the tissue is severed using a cutting element.

SUMMARY

As used herein, the term "distal" refers to the portion that is being described which is further from an operator (whether a human surgeon or a surgical robot), while the term "proximal" refers to the portion that is being described which is closer to the operator. The terms "about," substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is an end effector assembly of a surgical instrument including first and second jaw members at least one of which is movable relative to the other between a spaced-apart position and an approximated position to grasp tissue between opposing tissue contacting surfaces thereof. Each of the first and second jaw members includes a proximal flange portion and a distal body portion, and each of the proximal flange portions includes at least one pivot aperture disposed axially behind the distal body portion of the second jaw member that are aligned for receiving a pivot pin therethrough. The proximal flange portions are pivotably coupled to one another about the pivot pin.

In an aspect of the present disclosure, the proximal flange portion of the first jaw member includes a single flange defining a pivot aperture therethrough, and the proximal flange portion of the second jaw member includes a pair of spaced-apart flanges defining aligned pivot apertures therethrough. The single flange of the first jaw member is disposed between the pair of spaced-apart flanges of the second jaw member.

In another aspect of the present disclosure, the proximal flange portion of the first jaw member further includes a cam slot defined therethrough. The cam slot is configured to slidably receive a cam pin therein for transitioning the first and second jaw members between the spaced-apart and approximated positions. The proximal flange portion of the first jaw member may include a lip extending around the cam slot. The lip may extend tangentially outward from a side surface of a plate-shaped flange of the proximal flange portion.

In yet another aspect of the present disclosure, the second jaw member includes an internal spacer disposed on a distal portion of a structural jaw and an electrically-conductive plate disposed on the internal spacer. The structural jaw includes a proximal portion forming the proximal flange portion of the second jaw member. The electrically-conductive plate may define the tissue contacting surface of the second jaw member, and the tissue contacting surface may define a longitudinally extending knife channel therethrough. The internal spacer may include a partially-cylindrical cut-out in communication with the longitudinally extending channel defined through the electrically-conductive plate. The partially-cylindrical cut-out may have a generally D-shaped configuration and may be open at a proximal end of the internal spacer to permit insertion of a knife blade and a knife rod therethrough.

In still another aspect of the present disclosure, the internal spacer includes a wing extending from a side edge thereof in spaced relation relative to a side surface of the internal spacer. The wing of the internal spacer may be disposed between the structural jaw and the electrically-conductive plate, and an electrical lead may be attached to a portion of the electrically-conductive plate positioned over the wing.

In yet another aspect of the present disclosure, the first jaw member includes an internal spacer disposed on a distal portion of a structural jaw and an electrically-conductive plate disposed on the internal spacer. The structural jaw includes a proximal portion forming the proximal flange portion of the first jaw member. The electrically-conductive plate of the first jaw member may define the tissue contacting surface of the first jaw member, and the tissue contacting surface may define a longitudinally extending knife channel therethrough.

In still another aspect of the present disclosure, the internal spacer of the first jaw member includes a wing extending from a side edge thereof in spaced relation relative to a side surface of the internal spacer. The wing of the internal spacer of the first jaw member may be disposed between the structural jaw and the electrically-conductive plate of the first jaw member, and an electrical lead wire may be attached to a portion of the electrically-conductive plate of the first jaw member positioned over the wing.

In another aspect of the present disclosure, the first jaw member includes an outer housing disposed about the internal spacer, a distal portion of the structural jaw, and a portion of the electrically-conductive plate. The outer housing of the first jaw member may include a plate extending over a portion of the proximal flange portions of the first and second jaw members.

A surgical instrument provided in accordance with aspects of the present disclosure includes the end effector assembly described above and a shaft extending proximally from the end effector assembly. The shaft includes a distal segment within which the proximal flange portions of the end effector assembly are disposed. The surgical instrument may further include a housing extending proximally from the shaft. The housing may include an actuation assembly operably associated with the shaft and the end effector assembly. The actuation assembly may include a plurality of inputs configured to operably interface with a robotic surgical system.

Another end effector assembly of a surgical instrument provided in accordance with aspects of the present disclosure includes a first jaw member pivotably coupled to a second jaw member. The first jaw member includes: a first structural jaw; a first internal spacer disposed on the first structural jaw, the first internal spacer including a first wing extending from a side edge thereof in spaced relation relative to a side surface of the first internal spacer; a first electrically-conductive plate disposed on the first internal spacer, the first electrically-conductive plate having a first tissue contacting surface defining a first longitudinally extending knife channel therethrough; and a first outer housing disposed about the first internal spacer, a portion of the first structure jaw, and a portion of the first electrically-conductive plate.

In an aspect of the present disclosure, a first electrical lead wire is attached to a portion of the first electrically-conductive plate positioned over the first wing of the first internal spacer.

In another aspect of the present disclosure, the second jaw includes: a second structural jaw; a second internal spacer disposed on the second structural jaw, the second internal spacer including a second wing extending from a side edge thereof in spaced relation relative to a side surface of the second internal spacer; a second electrically-conductive plate disposed on the second internal spacer, the second electrically-conductive plate having a second tissue contacting surface defining a second longitudinally extending knife channel therethrough; and a second outer housing disposed about the second internal spacer, a portion of the second structure jaw, and a portion of the second electrically-conductive plate.

In yet another aspect of the present disclosure, a second electrical lead wire is attached to a portion of the second electrically-conductive plate positioned over the second wing of the second internal spacer.

In still another aspect of the present disclosure, the second internal spacer includes a partially-cylindrical cut-out in communication with the second longitudinally extending knife channel defined through the second electrically-conductive plate. The partially-cylindrical cut-out may have a generally D-shaped configuration and may be open at a proximal end of the second internal spacer to permit insertion of a knife blade and a knife rod therethrough.

In another aspect of the present disclosure, a distal portion of the first structural jaw, the first internal spacer, the first outer housing, and the first electrically-conductive plate form a distal body portion of the first jaw member, and a proximal portion of the first structural jaw forms a proximal flange portion of the first jaw member.

In yet another aspect of the present disclosure, a distal portion of the second structural jaw, the second internal spacer, the second outer housing, and the second electrically-conductive plate form a distal body portion of the second jaw member, and a proximal portion of the second structural jaw forms a proximal flange portion of the second jaw member.

In still another aspect of the present disclosure, the proximal flange portions of the first and second jaw members are pivotably coupled to one another about a pivot pin. Each of the proximal flange portions may include at least one pivot aperture disposed axially behind the distal body portion of the second jaw member, and the pivot apertures may be aligned for receiving the pivot pin therethrough.

In another aspect of the present disclosure, the proximal flange portion of the first jaw member includes a single flange defining a pivot aperture therethrough, and the proximal flange portion of the second jaw member includes a pair of spaced-apart flanges defining aligned pivot apertures therethrough. The single flange of the first jaw member is disposed between the pair of spaced-apart flanges of the second jaw member.

In an aspect of the present disclosure, the proximal flange portion of the first jaw member further includes a cam slot defined therethrough, the cam slot configured to slidably receive a cam pin. The proximal flange portion of the first jaw member may include a lip extending around the cam slot. The lip may extend tangentially outward from a side surface of a plate-shaped flange of the proximal flange portion.

A surgical instrument provided in accordance with aspects of the present disclosure includes the end effector assembly described above and a shaft extending proximally from the end effector assembly. The shaft includes a distal segment within which proximal flange portions of the end effector assembly are disposed, and the first and second jaw members are pivotably coupled to one another and the distal segment of the shaft via a pivot pin extending through the proximal flange portions and the distal segment.

In an aspect of the present disclosure, the first outer housing of the first jaw member includes a plate extending over a portion of the proximal flange portions of the first and second jaw members.

In another aspect of the present disclosure, a housing extends proximally from the shaft. The housing includes an actuation assembly operably associated with the shaft and the end effector assembly.

In yet another aspect of the present disclosure, the surgical instrument further includes a cam-slot assembly including a cam slot defined in the proximal flange portion of at least one of the first or second jaw members, a cam pin slidably received within the cam slot, and a cam bar coupled to the cam pin. The cam bar extends from the housing, through the shaft, and into the end effector assembly.

In still another aspect of the present disclosure, the surgical instrument further includes a knife assembly including a knife blade coupled to a distal end of a knife rod, the knife rod extending from the housing, through the shaft, and into the end effector assembly.

In yet another aspect of the present disclosure, the actuation assembly includes a plurality of inputs configured to operably interface with a robotic surgical system.

BRIEF DESCRIPTION OF THE DRAWINGS

Various aspects and features of the present disclosure are described hereinbelow with reference to the drawings wherein:

FIG. 5 is a side perspective view of the first and second jaw members of FIG. 3 with a distal segment of a shaft of the surgical instrument of FIG. 1 separated therefrom;

FIGS. 6A and 6B are side perspective views of a proximal flange portion of a first jaw member in accordance with aspects of the present disclosure;

FIG. 12A is a side view of a first jaw member of the surgical instrument of FIG. 1 in accordance with aspects of the present disclosure;

FIG. 12B is a perspective view of first and second jaw members of the surgical instrument of FIG. 1 in accordance with aspects of the present disclosure.

DETAILED DESCRIPTION

Figure 1:
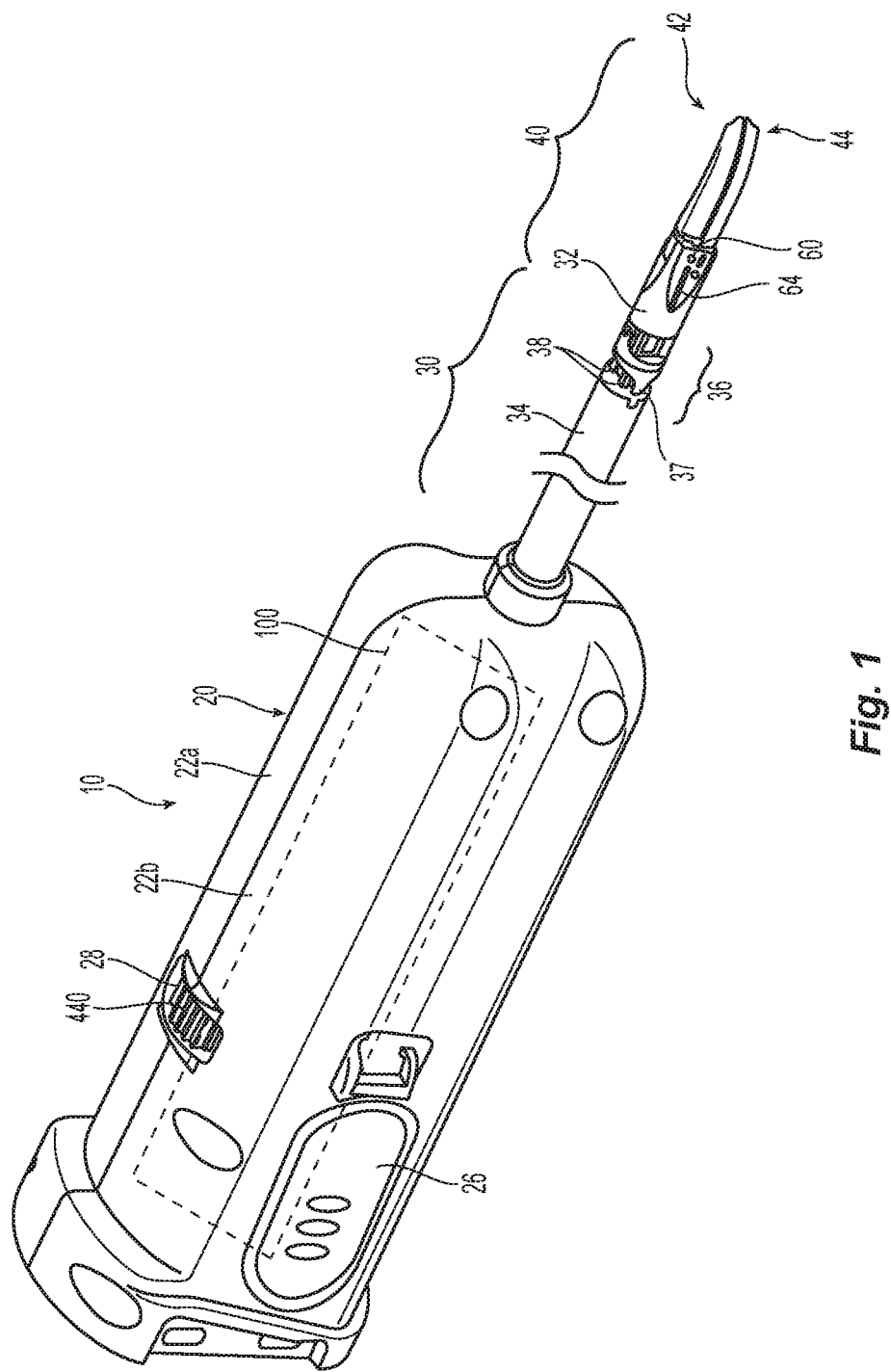
FIG. 1 is a perspective view of a surgical instrument in accordance with the present disclosure configured for mounting on a robotic arm of a robotic surgical system.
Figure 2:
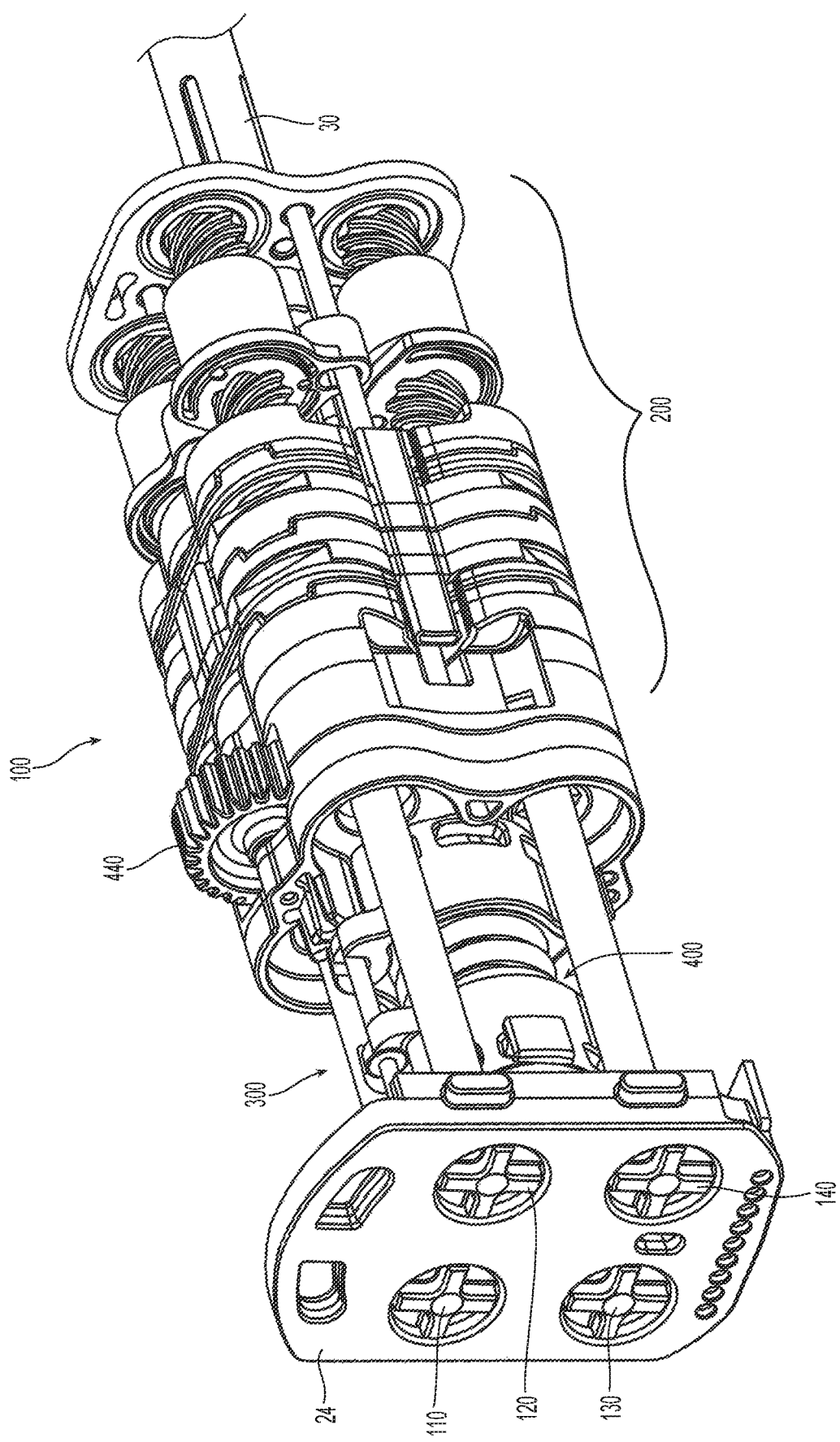
FIG. 2 is a rear perspective view of a proximal portion of the surgical instrument of FIG. 1 with an outer housing removed.
Figure 13:
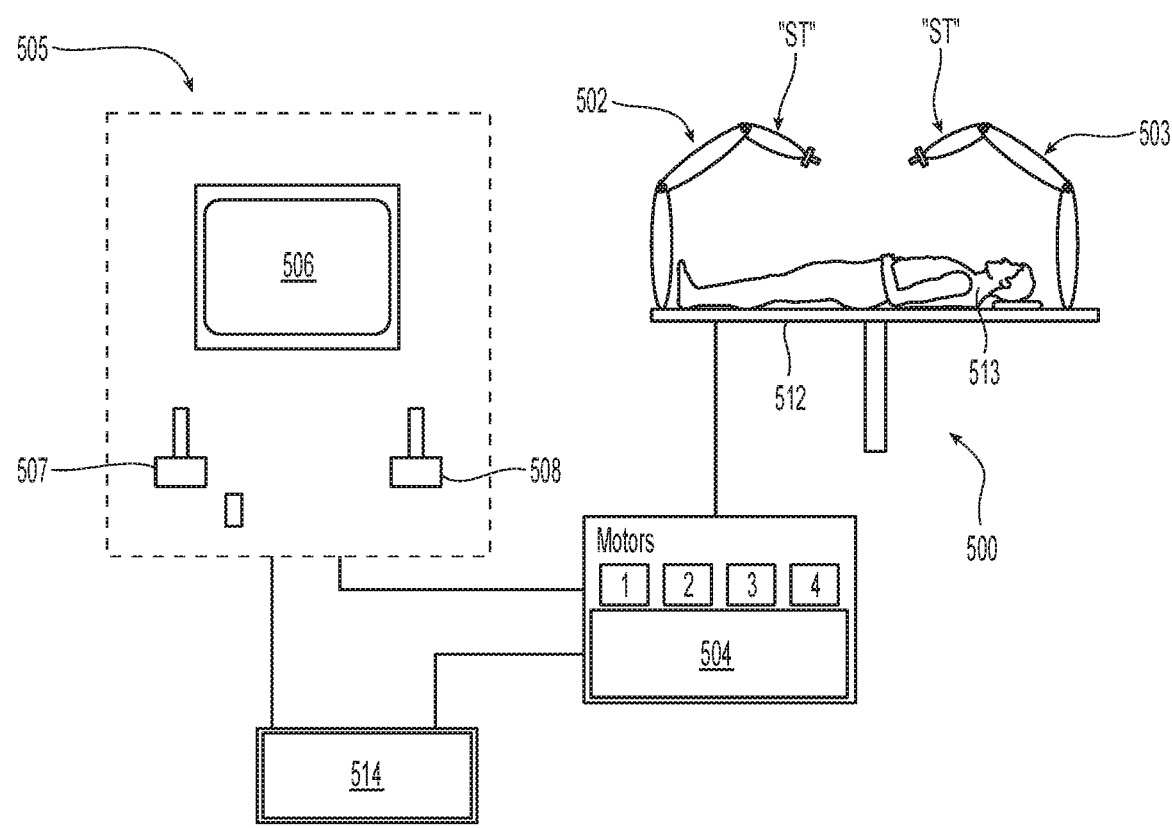
FIG. 13 is a schematic illustration of an exemplary robotic surgical system configured to releasably receive the surgical instrument of FIG. 1.

Referring to FIGS. 1 and 2, a surgical instrument 10 provided in accordance with the present disclosure generally includes a housing 20, a shaft 30 extending distally from the housing 20, an end effector assembly 40 extending distally from the shaft 30, and an actuation assembly 100 disposed within the housing 20 and operably associated with the shaft 30 and the end effector assembly 40. The surgical instrument 10 is detailed herein as an articulating electrosurgical forceps configured for use with a robotic surgical system, e.g., robotic surgical system 500 (FIG. 13). However, the aspects and features of the surgical instrument 10 provided in accordance with the present disclosure, detailed below, are equally applicable for use with other suitable surgical instruments (including non-robotic surgical instrument) and/or in other suitable surgical systems (including non-robotic surgical systems).

The housing 20 of the surgical instrument 10 includes first and second body portions 22a, 22b and a proximal faceplate 24 (FIG. 2) that cooperate to enclose the actuation assembly 100 therein. The proximal faceplate 24 includes apertures defined therein through which inputs 110, 120, 130, 140 of the actuation assembly 100 extend. A pair of latch levers 26 (only one of which is illustrated in FIG. 1) extends outwardly from opposing sides of the housing 20 and enables releasable engagement (directly or indirectly) of the housing 20 with a robotic arm of a surgical system, e.g., robotic surgical system 500 (FIG. 13). An aperture 28 defined through the housing 20 permits a thumbwheel 440 to extend therethrough to enable manual manipulation of the thumbwheel 440 from the exterior of the housing 20 to permit manual opening and closing of the end effector assembly 40.

The shaft 30 of the surgical instrument 10 includes a distal segment 32 (such as, for example, a collar or clevis), a proximal segment 34, and an articulating section 36 disposed between the distal and proximal segments 32, 34, respectively. The articulating section 36 includes one or more articulating components 37, e.g., links, joints, etc. A plurality of articulation cables 38, e.g., four (4) articulation cables, or other suitable actuators, extends through the articulating section 36. More specifically, the articulation cables 38 are operably coupled to the distal segment 32 of the shaft 30 at the distal ends thereof and extend proximally from the distal segment 32 of the shaft 30, through the articulating section 36 and the proximal segment 34 of the shaft 30, and into the housing 20, wherein the articulation cables 38 operably couple with an articulation assembly 200 of the actuation assembly 100 to enable selective articulation of the distal segment 32 (and, thus the end effector assembly 40) relative to the proximal segment 34 and the housing 20, e.g., about at least two axes of articulation (yaw and pitch articulation, for example). The articulation assembly 200 is operably coupled between the first and second inputs 110, 120, respectively, of the actuation assembly 100 and the articulation cables 38 (FIG. 1) such that, upon receipt of appropriate rotational inputs into the first and/or second inputs 110, 120, the articulation assembly 200 manipulates the articulation cables 38 to articulate the end effector assembly 40 in a desired direction, e.g., to pitch and/or yaw the end effector assembly 40. The articulation cables 38 are arranged in a generally rectangular configuration, although other suitable configurations are also contemplated.

With respect to articulation of the end effector assembly 40 relative to the proximal segment 34 of the shaft 30, actuation of the articulation cables 38 is effected in pairs. More specifically, in order to pitch the end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

Figure 3:
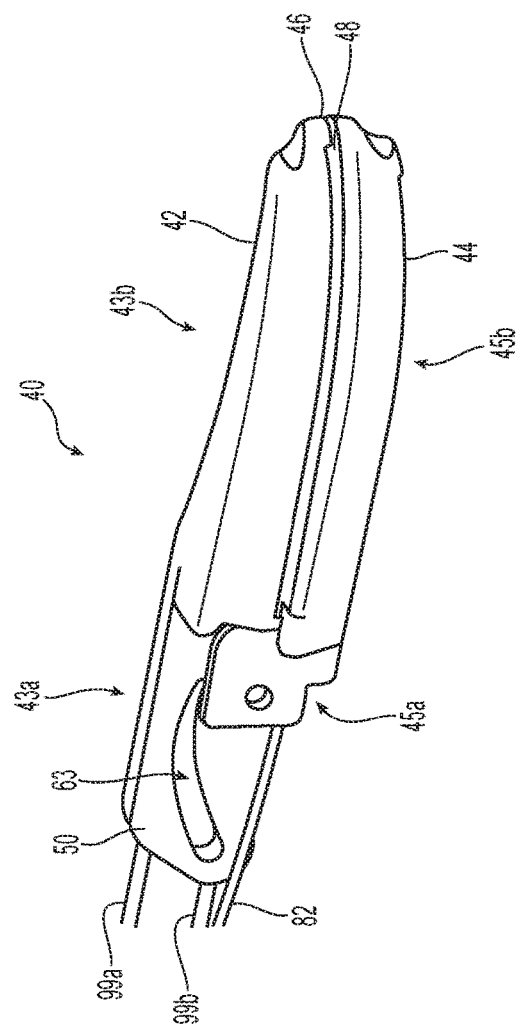
FIG. 3 is a perspective view of first and second jaw members of the surgical instrument of FIG. 1.
Figure 4:
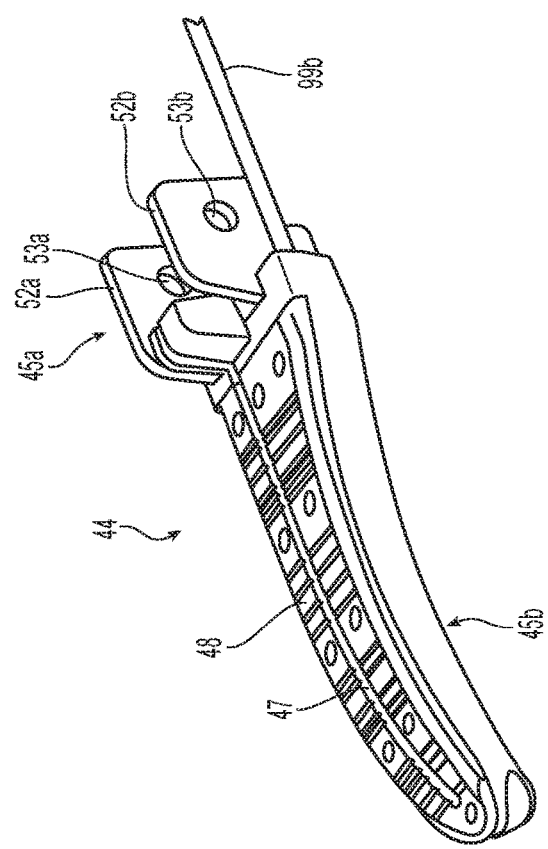
FIG. 4 is a perspective view of the second jaw member of FIG. 3.

With reference to FIGS. 3-5, the end effector assembly 40 includes first and second jaw members 42, 44, respectively. Each of the first and second jaw members 42, 44 includes a proximal flange portion 43a, 45a and a distal body portion 43b, 45b, respectively. Proximal flange portions 43a, 45a are pivotably coupled to one another about a pivot pin 60 (FIG. 1) and are operably coupled to one another via a cam-slot assembly 62 (FIG. 5). The cam-slot assembly 62 includes a cam pin 64 (FIG. 1) slidably received within cam slot(s) 63 defined within at least one of the proximal flange portions 43a, 45a of the first and second jaw members 42, 44, respectively, to enable pivoting of the first jaw member 42 relative to the second jaw member 44. Pivoting of the first jaw member 42 relative to the second jaw member 44 moves the distal body portions 43b, 45b between a spaced-apart position (e.g., an open position of the end effector assembly 40) and an approximated position (e.g. a closed position of the end effector assembly 40) for grasping tissue between tissue-contacting surfaces 46, 48 of the first and second jaw members 42, 44, respectively. As an alternative to this unilateral configuration, a bilateral configuration may be provided whereby both the first and second jaw members 42, 44 are pivotable relative to one another and the distal segment 32 of shaft 30.

As seen in FIGS. 3 and 4, the proximal flange portion 43a of the first jaw member 42 has a single plate-shaped flange 50 defining a pivot aperture 51 (FIG. 6A) therethrough and an angled or curved clam slot 63 extending through and along a length thereof. The proximal flange portion 45a of the second jaw member 44 includes a pair of spaced-apart plate-shaped flanges 52a, 52b defining aligned pivot apertures 53a, 53b, respectively, therethrough. The proximal flange portions 43a, 45a are configured so that the flange 50 of the first jaw member 42 is positionable between the flanges 52a, 52b of the second jaw member 44 with the pivot aperture 51 of the first jaw member 42 aligned with the pivot apertures 53a, 53b of the second jaw member 44.

The pivot apertures 53a, 53b of the second jaw member 44 are defined in a portion of the proximal flange portion 45a axially behind the distal body portion 45b to minimize the dead space in the distal segment 32 of the shaft 30 in which the proximal flange portions 43a, 45a are disposed. In aspects, the pivot apertures 53a, 53b of the second jaw member 44 are disposed in a lower half of the proximal flange portion 45a directly behind the distal body portion 45b, and the pivot aperture 51 of the proximal flange portion 43a of the first jaw member 42 is disposed in a position configured to align with the pivot apertures 53a, 53b of the second jaw member 44 when received therebetween. The pivot pin 50 (FIG. 1) is inserted through the pivot apertures 51, 53a, 53b, as well as through a pivot aperture 31 defined through the distal segment 32 of the shaft 30, to pivotably couple the first and second jaw member 42, 44 to the shaft 30 and to one another.

With continued reference to FIG. 5, the cam-slot assembly 62 includes a cam bar 66 having a distal end portion 66a coupled to a block 68, and a cam pin 64 extending outwardly from opposing lateral sides of the block 68. The block 68 defines an annular cutout 69 configured to receive the pivot pin 60 (FIG. 1) when the cam bar 66 is in a distal, deployed position. The annular cutout 69, therefore, allows full distal translation of the cam bar 66 without interference from the pivot pin 60. A first end of the cam pin 64 is received in a linear cam slot 33 of the distal segment 32 of the shaft 30 to guide and support a linear movement of the cam bar 66, and a second end of the cam pin 64 (not explicitly shown) is received in the cam slot 63 of the proximal flange portion 43a of first jaw member 42.

The cam slot 63 in the proximal flange portion 43a of the first jaw member 42 is shaped such that advancement (e.g., distal translation) of the cam bar 66 relative to the proximal flange portion 43a causes the cam pin 64 to ride distally through the cam slot 63 and drives a pivoting of the first jaw member 42 away from the second jaw member 44 to transition the end effector assembly 40 from the closed position to the open position. Similarly, retraction (e.g., proximal translation) of the cam bar 66 relative to the proximal flange portion 43a causes the cam pin 64 to ride proximally through the cam slot 63 and drives a pivoting of the first jaw member 42 towards the second jaw member 44 to transition the end effector assembly 40 from the open position to the closed position for grasping tissue between the tissue-contacting surfaces 46, 48. Alternatively, the cam bar 66 may be moved distally to transition the end effector assembly 40 to the closed position and proximally to transition the end effector assembly 40 to the open position.

The cam bar 66 extends proximally from the end effector assembly 40 through the shaft assembly 30 and into the housing 20 wherein the cam bar 66 is operably coupled with a jaw drive assembly 400 (FIG. 2) of the actuation assembly 100 to enable selective actuation of the end effector assembly 40. The jaw drive assembly 400 is operably coupled between the fourth input 140 of the actuation assembly 100 and the cam bar 66 such that, upon receipt of appropriate rotational input into the fourth input 140, the jaw drive assembly 400 pivots the first and second jaw members 42, 44 between the open and closed positions to grasp tissue therebetween and apply a closure force within an appropriate closure force range.

In aspects, as shown in FIGS. 6A and 6B, the proximal flange portion 43a of the first jaw member 42 includes a lip 41 extending around the cam slot 63. The lip 41 extends tangentially outward from a side surface of the proximal flange portion 43a around the entirety of the cam slot 63 to increase cam slot strength and/or reduce clam slot stress, for example, if the proximal flange portion 43a has a thin-wall construction and/or the first and second jaw members 42, 44 are exposed to a heavy load. The lip 41, however, may have other configurations. For example, the lip 41 may be discontinuous and extend along opposed sides and/or ends of the cam slot 63, such as around a proximal end portion of the cam slot 63 coinciding with closing of the first and second jaw members 42, 44 (or a distal end portion of the cam slot 63 in aspects where the cam bar 66 is moved distally for closing of the first and second jaw members 42, 44). As another example, the lip 41 may extend outwardly from both side surfaces of the proximal flange portion 43a.

Turning again to FIGS. 3 and 4, the distal body portions 43b, 45b of the first and second jaw members 42, 44 define opposed tissue-contacting surfaces 46, 48, respectively. The tissue contacting surfaces 46, 48 are at least partially formed from an electrically conductive material and are energizable to different potentials to enable the conduction of electrical energy through tissue grasped therebetween, although the tissue contacting surfaces 46, 48 may alternatively be configured to supply any suitable energy, e.g., thermal, microwave, light, ultrasonic, etc., through tissue grasped therebetween for energy-based tissue treatment. The surgical instrument 10 (FIG. 1) defines a conductive pathway (not shown) through the housing 20 and the shaft 30 to the end effector assembly 40 that includes electric lead wires 99a, 99b, contacts, and/or electrically-conductive components to enable electrical connection of the tissue contacting surfaces 46, 48 of the first and second jaw members 42, 44, respectively, to an energy source (not shown), e.g., an electrosurgical generator via an electrosurgical cable extending therebetween, for supplying energy to the tissue contacting surfaces 46, 48 to treat, e.g., seal, tissue grasped between the tissue contacting surfaces 46, 48.

Figure 7:
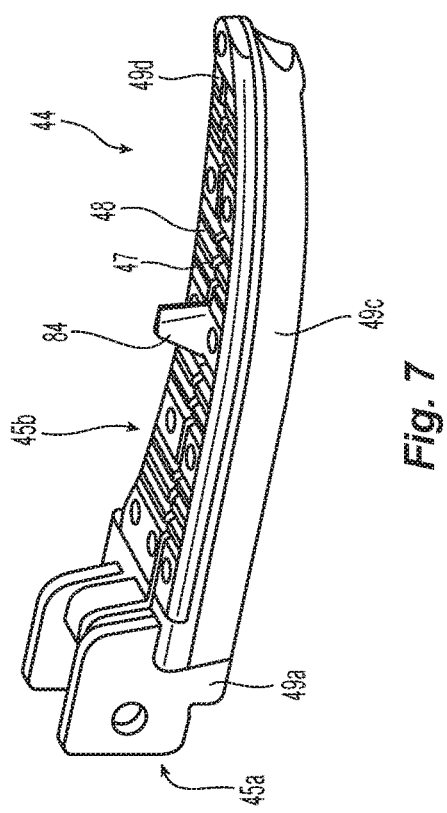
FIG. 7 is a side perspective view of the second jaw member of FIG. 4 with a knife blade of the surgical instrument of FIG. 1.
Figure 8B:
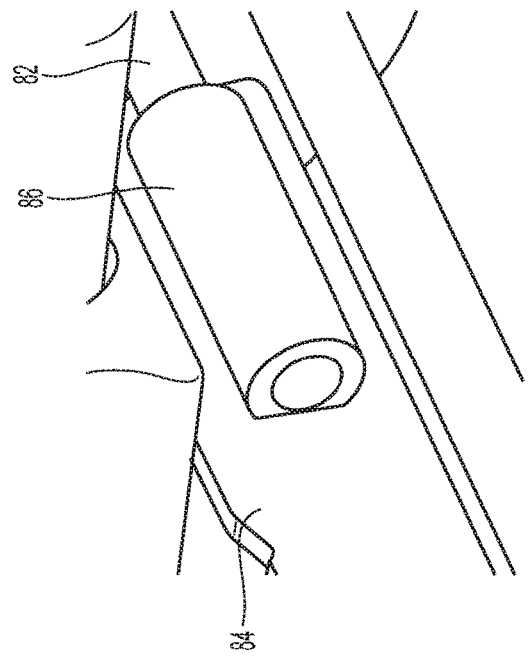
FIGS. 8A and 8B are perspective views of a knife assembly of the surgical instrument of FIG. 1.

The tissue contacting surfaces 46, 48 each define a longitudinally extending knife channel 47 (only the knife channel 47 of the second jaw member 44 is explicitly seen in FIG. 4). As shown in FIGS. 7-8B, a knife assembly 80 is provided that includes a knife rod 82 and a knife blade 84 fixed to or otherwise coupled to a distal end of the knife rod 82. The knife assembly 80 enables cutting of tissue grasped between tissue contacting surfaces 46, 48 of the first and second jaw members 42, 44, respectively. A ferrule 86 may be engaged about a distal end portion of the knife rod 82 and secured within a slot 83 defined within a proximal portion of the knife blade 84 to securely engage the knife rod 82 with the knife blade 84 such that actuation of the knife rod 82 reciprocates the knife blade 84 between the first and second jaw member 42, 44 to cut tissue grasped between the tissue contacting surfaces 46, 48. The knife rod 82 and the ferrule 86 are offset relative to the knife blade 84 such that the knife rod 82 and the ferrule 86 protrude farther (or completely) from one side of the knife blade 84 and less (or not at all) from the other side.

The knife rod 82 extends from the housing 20 (FIG. 1) through the shaft 30 to the end effector assembly 40. The knife rod 82 is operably coupled to a knife drive assembly 300 (FIG. 2) of the actuation assembly 100 for selective actuation of the knife assembly 80 to reciprocate the knife blade 84 through the first and second jaw members 42, 44. The knife drive assembly 300 (FIG. 2) is operably coupled between the knife rod 82 of the knife assembly 80 and the third input 130 of the actuation assembly 100 such that, upon receipt of appropriate rotational input into the third input 130, the knife drive assembly 300 manipulates the knife rod 82 to reciprocate the knife blade 84 between the first and second jaw members 42, 44 to cut tissue grasped between the tissue contacting surfaces 46, 48.

Figure 9B:
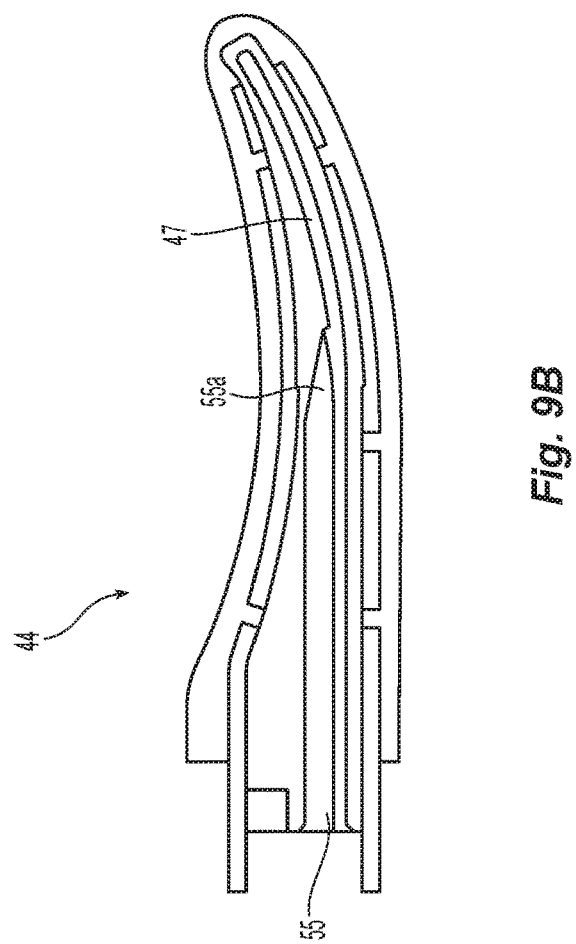
FIG. 9B is a cross-sectional view of the second jaw member of FIG. 9A, taken along section line 9B-9B of FIG. 9A.
Figure 9A:
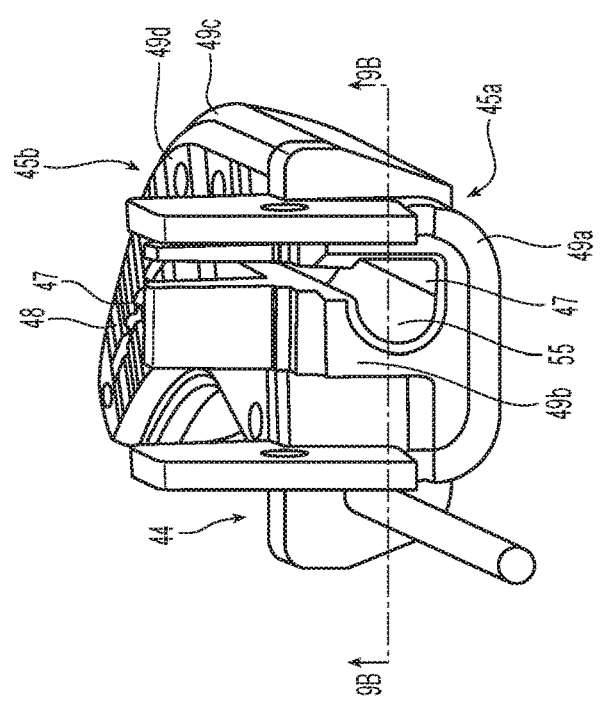
FIG. 9A is a proximal end view of the second jaw member of FIG. 4.

Turning now to FIG. 9A, the second jaw member 44 is shown. The second jaw member 44, as noted above, includes proximal flange portion 45a and distal body portion 45b. The second jaw member 44, more specifically, includes a structural jaw 49a, an internal spacer 49b (e.g., an insulative spacer), an outer housing 49c, and an electrically-conductive plate 49d defining the tissue contacting surface 48. It should be understood that the first jaw member 42 is configured similar to the second jaw member 44 and includes similar component parts (e.g., a structural jaw, an internal spacer, an outer housing, and an electrically-conductive plate).

The structural jaw 49a provides structural support to second jaw member 44 and includes a distal portion that supports the components of the distal body portion 45b of the second jaw member 44 thereon and a proximal portion that extends proximally from the distal body portion 45b to form the proximal flange portion 45a of the second jaw member 44. The distal portion of the structural jaw 49a, together with the internal spacer 49b, the outer housing 49c, and the electrically-conductive plate 49d, form the distal body portion 45b of the second jaw member 44. The internal spacer 49b is disposed on the distal portion of the structural jaw 49a, the electrically-conductive plate 49d is disposed on the internal spacer 49b, and the outer housing 49c is disposed about the internal spacer 49b, the distal portion of the structural jaw 49a, and a portion of the electrically-conductive plate 49d to secure these components to one another, e.g., via overmolding, although other configurations are also contemplated.

Figure 8A:
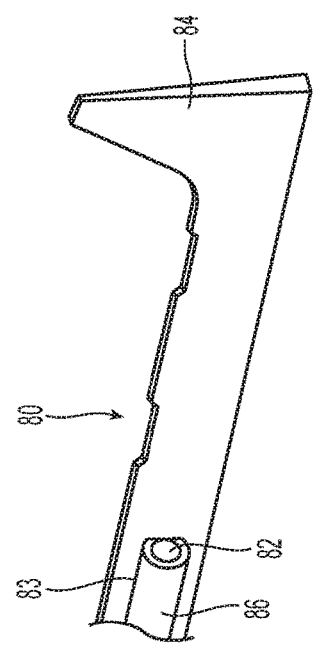

The longitudinally extending channel 47 of the second jaw member 44 is formed by cooperating channel portions defined within the electrically-conductive plate 49d and the internal spacer 49b. The internal spacer 49b further includes a partially-cylindrical cut-out 55 that communicates with the longitudinally extending channel 47. The cut-out 55 has a generally D-shaped configuration and is open at the proximal end of the distal body portion 45b of the second jaw member 44 to permit insertion of the knife blade 84, and the knife rod 82 and ferrule 86 (FIG. 8B) therethrough. As shown in FIG. 9B, the cut-out 55 has a ramped distal end 55a tapering laterally inwardly towards the longitudinal extending channel 47 for preventing tissue from entering the second jaw member 44 (e.g., pushing or ejecting tissue out of the longitudinally extending channel 47 when the knife blade 84 is deployed). It should be understood that the cut-out 55 may have other shapes depending, for example, on the configuration of the knife assembly 80 (FIG. 8A).

Figure 10A:
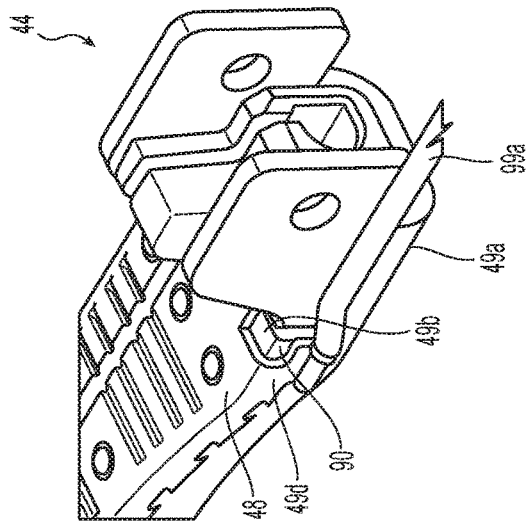
FIG. 10A is a rear perspective view of an internal spacer of the second jaw member of FIG. 9A.
Figure 10B:
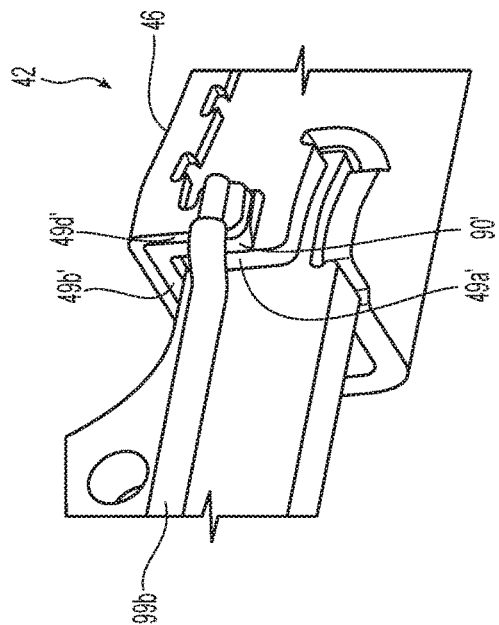
FIG. 10B is a rear perspective view of the second jaw member of FIG. 9A, shown with an outer housing of the second jaw member removed.

As shown in FIGS. 10A and 10B, in conjunction with FIG. 9A, the internal spacer 49b of the second jaw member 44 includes a wing 90 extending from a side edge 57a thereof. The wing 90 extends downwardly from the side edge 57a of a top surface 57b on which the electrically-conductive plate 49d is disposed such that the wing 90 is in spaced relation relative to a side surface 57c of the internal spacer 49b. A gap "G1" defined between the wing 90 and the internal spacer 49b is sized and shaped to accommodate the structural jaw 49a therein to separate the structural jaw 49a from the electrically-conductive plate 49d. The electrical lead wire 99a that electrically connects the tissue contacting surface 48 to the energy source (not shown) is attached to the portion of the electrically-conductive plate 49d extending over the wing 90. The wing 90 extends from a portion of the internal spacer 49b that covers and isolates the attachment location (e.g., a wire weld strip) of the electrical lead wire 99a to the electrically-conductive plate 49d.

Figure 11A:
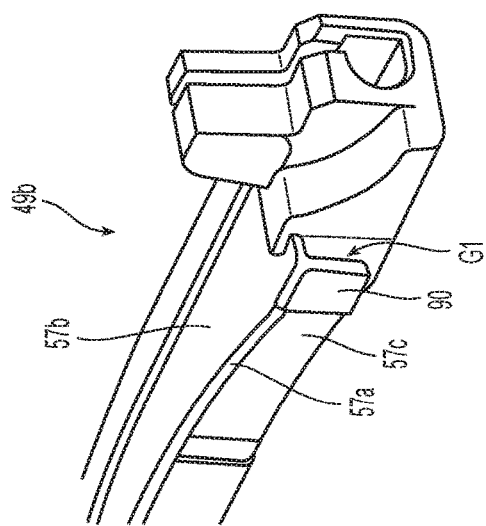
FIG. 11A is a side perspective view of an internal spacer of the first jaw member of FIG. 3.
Figure 11B:
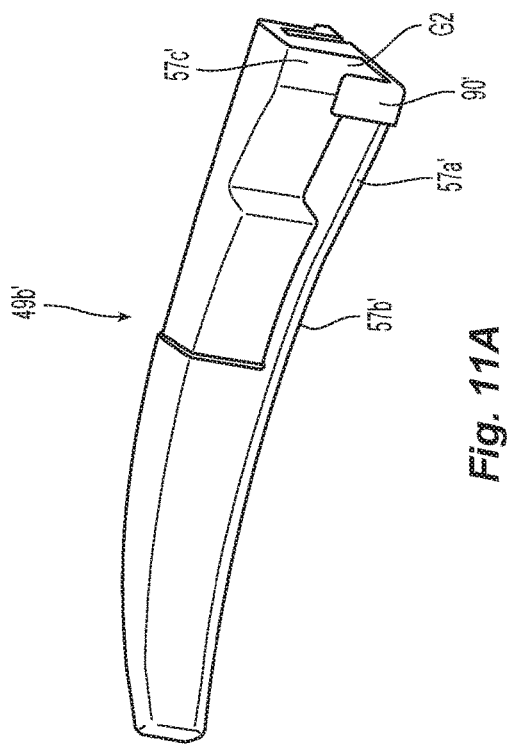
FIG. 11B is a side perspective view of the first jaw member of FIG. 3, shown with an outer housing of the first jaw member removed.

As shown in FIGS. 11A and 11B, the internal spacer 49b' of the first jaw member 42 similarly includes a wing 90' extending from a side edge 57a' thereof. The wing 90' extends downwardly from the side edge 57a' of a top surface 57b' on which an electrically-conductive plate 49d' is disposed such that the wing 90' is in spaced relation relative to a side surface 57c' of the internal spacer 49b'. A gap "G2" defined between the wing 90' and the internal spacer 49b' is sized and shaped to accommodate the structural jaw 49a' therein to separate the structural jaw 49a' from the electrically-conductive plate 49d'. The electrical lead wire 99b that electrically connects the tissue contacting surface 46 to the energy source (not shown) is attached to the portion of the electrically-conductive plate 49d' extending over the wing 90'. The wing 90' extends from a portion of the internal spacer 49b' that covers and isolates the attachment location (e.g., a wire weld strip) of the electrical lead wire 99b to the electrically-conductive plate 49d'.

As shown in FIGS. 12A and 12B, the first jaw member 42 may further include a plate 92 extending over a gap "G" defined between the distal segment 32 of the shaft 30 and the distal body portion 43b of the first jaw member 42. The plate 92 covers the gap "G" and thus, the proximal flange portions 43a, 45a of the first and second jaw members 42, 44 and the knife blade 84, minimizing tissue build up that may otherwise occur in the gap "G" and reducing pinch point between the first and second jaw members 42, 44. The plate 92 may be coupled to or integrally formed with the outer housing 49c of the first jaw member 42 e.g., via overmolding, although other configurations are also contemplated.

Turning now to FIG. 13, a robotic surgical system 500 is configured for use in accordance with the present disclosure. Aspects and features of the robotic surgical system 500 not germane to the understanding of the present disclosure are omitted to avoid obscuring the aspects and features of the present disclosure in unnecessary detail.

The robotic surgical system 500 generally includes a plurality of robot arms 502, 503; a control device 504; and an operating console 505 coupled with control device 504. The operating console 505 may include a display device 506, which may be set up in particular to display three-dimensional images; and manual input devices 507, 508, by means of which a person, e.g., a surgeon, may be able to telemanipulate the robot arms 502, 503 in a first operating mode. The robotic surgical system 500 may be configured for use on a patient 513 lying on a patient table 512 to be treated in a minimally invasive manner. The robotic surgical system 500 may further include a database 514, in particular coupled to the control device 504, in which are stored, for example, pre-operative data from the patient 513 and/or anatomical atlases.

Each of the robot arms 502, 503 may include a plurality of members, which are connected through joints, and a mounted device which may be, for example, a surgical tool "ST." One or more of the surgical tools "ST" may be the surgical instrument 10 (FIG. 1), thus providing such functionality on a robotic surgical system 500.

Specifically, the actuation assembly 100 (FIG. 2) is configured to operably interface with the robotic surgical system 500 when the surgical instrument 10 is mounted on the robotic surgical system 500 to enable robotic operation of the actuation assembly 100. That is, the robotic surgical system 500 selectively provides rotational inputs to inputs 110, 120, 130, 140 of the actuation assembly 100 to articulate the end effector assembly 40, grasp tissue between the first and second jaw members 42, 44, and/or cut tissue grasped between the first and second jaw members 42, 44.

The robot arms 502, 503 may be driven by electric drives, e.g., motors, connected to the control device 504. The control device 504, e.g., a computer, may be configured to activate the motors, in particular by means of a computer program, in such a way that the robot arms 502, 503, and, thus, their mounted surgical tools "ST" execute a desired movement and/or function according to a corresponding input from the manual input devices 507, 508, respectively. The control device 504 may also be configured in such a way that it regulates the movement of the robot arms 502, 503 and/or of the motors.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended hereto.

What is claimed is:

1. An end effector assembly of a surgical instrument, comprising:
    a first jaw member including:
        a first structural jaw;
        a first internal spacer disposed on the first structural jaw, the first internal spacer including a first wing extending from a side edge thereof in spaced relation relative to a side surface of the first internal spacer;
        a first electrically-conductive plate disposed on the first internal spacer, the first electrically-conductive plate having a first tissue contacting surface defining a first longitudinally extending knife channel therethrough, the first structural jaw disposed within a gap defined between the first wing and the side surface of the first internal spacer, wherein the first electrically-conductive plate is configured to connect to a first electrical lead wire at a portion of the first electrically-conductive plate that is disposed laterally outward from the first wing such that the first wing is disposed between the side surface of the first internal spacer and the connection between the first electrical lead wire and the first electrically-conductive plate; and
        a first outer housing disposed about the first internal spacer, a portion of the first structure jaw, and a portion of the first electrically-conductive plate; and
    a second jaw member pivotably coupled to the first jaw member.

2. The end effector assembly of claim 1, wherein the second jaw member includes:
    a second structural jaw;
    a second internal spacer disposed on the second structural jaw, the second internal spacer including a second wing extending from a side edge thereof in spaced relation relative to a side surface of the second internal spacer;
    a second electrically-conductive plate disposed on the second internal spacer, the second electrically-conductive plate having a second tissue contacting surface defining a second longitudinally extending knife channel therethrough; and
    a second outer housing disposed about the second internal spacer, a portion of the second structure jaw, and a portion of the second electrically-conductive plate.

3. The end effector assembly of claim 2, further including a second electrical lead wire attached to a portion of the second electrically-conductive plate positioned over the second wing of the second internal spacer.

4. The end effector assembly of claim 2, wherein the second internal spacer includes a partially-cylindrical cut-out in communication with the second longitudinally extending knife channel defined through the second electrically-conductive plate.

5. The end effector assembly of claim 4, wherein the partially-cylindrical cut-out has a generally D-shaped configuration and is open at a proximal end of the second internal spacer to permit insertion of a knife blade and a knife rod therethrough.

6. The end effector assembly of claim 2, wherein a distal portion of the first structural jaw, the first internal spacer, the first outer housing, and the first electrically-conductive plate form a distal body portion of the first jaw member, and a proximal portion of the first structural jaw forms a proximal flange portion of the first jaw member.

7. The end effector assembly of claim 6, wherein a distal portion of the second structural jaw, the second internal spacer, the second outer housing, and the second electrically-conductive plate form a distal body portion of the second jaw member, and a proximal portion of the second structural jaw forms a proximal flange portion of the second jaw member.

8. The end effector assembly of claim 7, wherein the proximal flange portions of the first and second jaw members are pivotably coupled to one another about a pivot pin.

9. The end effector assembly of claim 8, wherein each of the proximal flange portions includes at least one pivot aperture disposed axially behind the distal body portion of the second jaw member, the pivot apertures aligned for receiving the pivot pin therethrough.

10. The end effector assembly of claim 9, wherein the proximal flange portion of the first jaw member includes a single flange defining a pivot aperture therethrough, and the proximal flange portion of the second jaw member includes a pair of spaced-apart flanges defining aligned pivot apertures therethrough, the single flange of the first jaw member disposed between the pair of spaced-apart flanges of the second jaw member.

11. The end effector assembly of claim 6, wherein the proximal flange portion of the first jaw member further includes a cam slot defined therethrough, the cam slot configured to slidably receive a cam pin.

12. The end effector assembly of claim 11, wherein the proximal flange portion of the first jaw member includes a lip extending around the cam slot.

13. The end effector assembly of claim 12, wherein the lip extends tangentially outward from a side surface of a plate-shaped flange of the proximal flange portion.

14. A surgical instrument, comprising:
    an end effector assembly including:
        a first jaw member including:
            a first structural jaw;
            a first internal spacer disposed on the first structural jaw, the first internal spacer including a first wing extending from a side edge thereof in spaced relation relative to a side surface of the first internal spacer;
            a first electrically-conductive plate disposed on the first internal spacer, the first electrically-conductive plate having a first tissue contacting surface defining a first longitudinally extending knife channel therethrough, the first structural jaw disposed within a gap defined between the first wing and the side surface of the first internal spacer, wherein the first electrically-conductive plate is configured to connect to a first electrical lead wire at a portion of the first electrically-conductive plate that is disposed laterally outward from the first wing such that the first wing is disposed between the side surface of the first internal spacer and the connection between the first electrical lead wire and the first electrically-conductive plate; and a first outer housing disposed about the first internal spacer, a portion of the first structure jaw, and a portion of the first electrically-conductive plate; and a second jaw member pivotably coupled to the first jaw member; and a shaft extending proximally from the end effector assembly, the shaft including a distal segment within which proximal flange portions of the end effector assembly are disposed, the first and second jaw members pivotably coupled to one another and the distal segment of the shaft via a pivot pin extending through the proximal flange portions and the distal segment.

15. The surgical instrument of claim 14, wherein the first outer housing of the first jaw member includes a plate extending over a portion of the proximal flange portions of the first and second jaw members.

16. The surgical instrument of claim 14, further including a housing extending proximally from the shaft, the housing including an actuation assembly operably associated with the shaft and the end effector assembly.

17. The surgical instrument of claim 16, further including a cam-slot assembly including a cam slot defined in the proximal flange portion of at least one of the first or second jaw members, a cam pin slidably received within the cam slot, and a cam bar coupled to the cam pin, the cam bar extending from the housing, through the shaft, and into the end effector assembly.

18. The surgical instrument of claim 16, further including a knife assembly including a knife blade coupled to a distal end of a knife rod, the knife rod extending from the housing, through the shaft, and into the end effector assembly.

* * * * *